United States Patent [19]
McClure

[11] 3,934,979
[45] Jan. 27, 1976

[54] METHOD OF ASSAY FOR PROSTAGLANDINS OF THE F ALPHA SERIES

[75] Inventor: William O. McClure, S. Pasadena, Calif.

[73] Assignee: Nelson Research & Development Co., Irvine, Calif.

[22] Filed: Oct. 7, 1974

[21] Appl. No.: 512,447

[52] U.S. Cl. ................................. 23/230 B; 424/7
[51] Int. Cl. ..................... G01n 21/00; G01n 31/08; G01n 33/16
[58] Field of Search ..................... 23/230 B; 424/7

[56] References Cited
OTHER PUBLICATIONS

N. Ambache et al., Brit. J. Pharmacol. 33, 162, (1968).
E. W. Horton, Physiological Review 49, No. 1, Jan. 1969, pp. 122+.
N. H. Andersen, Chem. Abstr. 71, 27642p (1969).
E. Anggard et al., J. Chromatogr. 48, 542, (1970).

*Primary Examiner*—Robert M. Reese
*Attorney, Agent, or Firm*—Martin A. Voet

[57] ABSTRACT

A method for assaying prostaglandins of the $F_\alpha$ series by reacting a compound of this series with a compound having the formula $R-B(OH)_2$ wherein R is a radical containing a fluorescent or radioactive label, isolating the reaction product and measuring the amount of fluorescence or radioactivity of the reaction product.

9 Claims, No Drawings

METHOD OF ASSAY FOR PROSTAGLANDINS OF THE F ALPHA SERIES

BACKGROUND OF THE INVENTION

1. Field of the Invention

The present invention relates to an assay. More particularly, the present invention relates to an assay for prostaglandins of the $F_\alpha$ series.

2. Background of the Prior Art

Prostaglandins of the $F_\alpha$ series are known and are characterized by containing a $C_9$ and $C_{11}$ cis-diol structure in the cyclopentane ring.

For example, prostaglandin $F_{2\alpha}$ ($PGF_{2\alpha}$) is a compound having the following structural formula

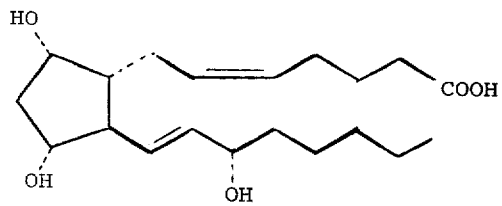

Other $F_\alpha$ prostaglandins include $PGF_{1\alpha}$ and $PGF_{3\alpha}$. Prostaglandins exist in the cells of many, if not all, animals. They exert biological activities in the body of the animal in which it is present. A simple assay for the presence of $PGF\alpha$ compounds, and especially $PGF_{2\alpha}$, would be valuable for research and diagnostic purposes.

It was disclosed in J. Chrom. Sci. 56 1:129 (1971) that n-butyl boronic acid reacts with $PGF_{2\alpha}$ and the combination may be used in the GLC analysis for $PGF_{2\alpha}$.

SUMMARY OF THE INVENTION

The present invention relates to a method for assaying for prostaglandins of the $F_\alpha$ series comprising reacting prostaglandins of the $F\alpha$ series with a compound having the formula

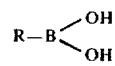

where R is a radical containing a fluorescent of radioactive label, isolating the labeled reaction product, and measuring the amount of fluorescence or radioactivity of the labeled reaction product.

DETAILED DESCRIPTION OF THE INVENTION

The following general reaction is utilized by the present assay method (in this case, $PGF_{2\alpha}$ is representative of prostaglandins of the $F_\alpha$ series).

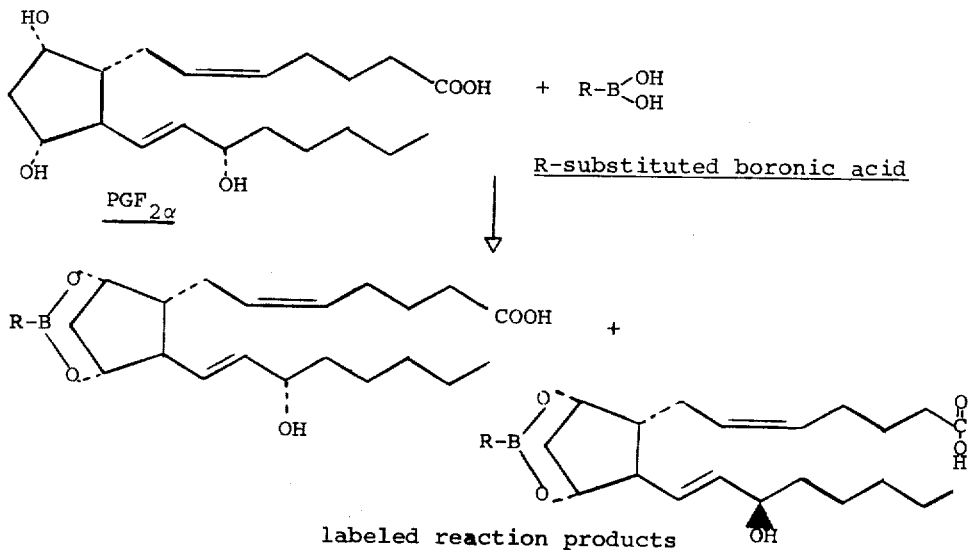

The radical R in the compound

R—B(OH)(OH)

can contain either a radioactive label or a fluorescent label. For example, R may be any radical containing a $^{14}C$ or $^{3}H$ or $S^{35}$ or $I^{131}$ or $I^{125}$ or other radioactive label. A preferred radioactive label is a labeled hydrocarbon radical such as, for example, an n-butyl group labeled with $^{14}C$ or $^{3}H$. Similarly, R could be any fluorescent radical such as, for example, in the following compounds:

(1) 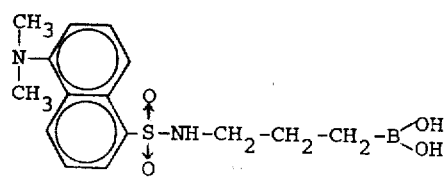

(2) 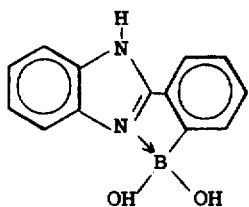

(3) 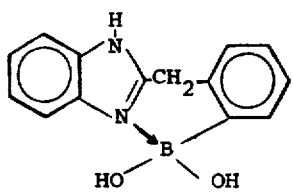

(4) 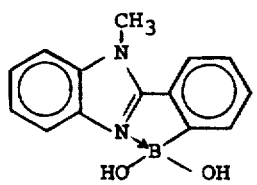

(5) 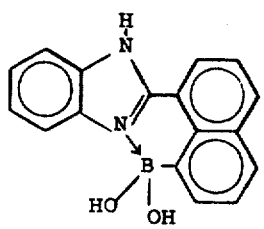

(6) 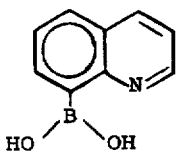

The reaction of the labeled boronic acid derivative and prostaglandins of the $F_\alpha$ series takes place in conventional organic solvents such as methanol, ethanol, butanol, acetone, 2,2-dimethoxypropane, etc.

Prior to the reaction, the prostaglandin of the $F_\alpha$ series is preferably extracted from whatever aqueous medium or biological fluid it is in by extraction with a suitable solvent, such as ethyl acetate, or by column chromatographic isolation utilizing, for example, Sephadex LH-20 or Amberlite XAD-2 columns.

The reaction of a prostaglandin of the $F_\alpha$ series and the boronic acid derivatives may be carried out at temperatures between about 20° and 100°C and preferably at about 50°C for about 1 to about 30 minutes and preferably about 1–5 minutes.

The labeled reaction products are then isolated from the reaction mixture by any suitable analytical method including thin layer chromatography (TLC), paper chromatography, column chromatography, etc.

The isolated, labeled reaction products are then evaluated for fluorescence (if the boronic acid derivative was labeled with a fluorescent-containing radical) by conventional fluorometric techniques or for radioactivity (if the boronic acid derivative was labeled with a radical containing a radioactive species) by conventional radiation counting.

The foregoing method results in a qualitative as well as quantitative assay for prostaglandins of the $F_\alpha$ series.

This assay may be used to determine levels of prostaglandins of the $F_\alpha$ series including various biological systems including biological tissues, blood, urine, etc. In order to guard against loss of a prostaglandin $F_\alpha$ in a sample, e.g. by degradation, an internal standard may be used. For example, a known amount of $^{14}C$ labeled $PGF_{2\alpha}$ may be added to the sample prior to the assay and counted at the end of the procedure. The percent reduction of $^{14}C$ $PGF_{2\alpha}$ from the known amount placed in the sample indicates the percent of $PGF_{2\alpha}$ lost during the assay procedure. Other similar internal standards may be used.

In order to minimize interference of background radiation caused by exchange of $^3H$ atoms (if a tritiated label is used) for $^1H$ atoms in water present in the assay sample, the water remaining in the reaction sample is preferably removed by any convenient method, e.g. a deliquescent substance such as, for example, magnesium sulfate, may be added to the sample.

The following Examples are for the purpose of illustration and it is understood that the invention is not to be limited to the reagents or conditions set forth.

EXAMPLE I

Assay for $PGF_{2\alpha}$ is conducted by reacting with $10^{-9}$ g $^3H$-labeled n-butyl boronic acid (10 C/m-mole) with $PGF_{2\alpha}$ at 50°C under anhydrous conditions in 2,2-dimethoxypropane for 1 minute. The reaction mixture is then spotted on silica gel TLC plates and developed in a solvent system consisting of the organic phase of ethyl acetate-glacial acetic acid-iso-octane-water in ratios of 110:20:50:100. The plates are visualized with $I_2$ vapor and the reaction product spot scraped and the radioactivity is measured by a standard scintillation counter. The results indicate that in excess of 90% of the $PGF_{2\alpha}$ is recovered.

EXAMPLE II

Example I is repeated in the presence of prostaglandin $E_2$ ($PGE_2$). No interference of the reaction by $PGE_2$ is found.

EXAMPLE III

EXAMPLE I is repeated, except the radioactive labeled boronic acid is replaced with the fluorescent compound

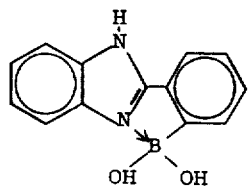

After the labeled reaction products are separated by TLC, they are analyzed by conventional fluorescent techniques instead of radioactive counting. Similar results are obtained.

EXAMPLE IV

EXAMPLE I is repeated, except the n-butyl boronic acid is labeled with $^{14}C$ rather than $^3H$. Comparable results are obtained.

I claim:

1. A method for assaying prostaglandins of the $F_\alpha$ series comprising reacting a prostaglandin of the $F_\alpha$ series with a compound having the formula $$R-B\begin{matrix}\diagup OH \\ \diagdown OH\end{matrix}$$

where R is a radical containing a fluorescent or radioactive label, isolating the labeled reaction products, and respectively measuring the amount of fluorescence or radioactivity of the labeled reaction product.

2. The method of claim 1 wherein R contains a fluorescent label.

3. The method of claim 1 wherein R contains a radioactive label.

4. The method of claim 2 wherein the radioactive label is $^{14}C$ or $^3H$.

5. The method of claim 1 wherein R is a tritium labeled butyl radical.

6. The method of claim 4 wherein the prostaglandin is prostaglandin $F_{2\alpha}$.

7. A method for assaying prostaglandin $F_{2\alpha}$ comprising reacting a biological sample containing $PGF_{2\alpha}$ with $^3H-CH_3-CH_2-CH_2-CH_2$ $$R-B\begin{matrix}\diagup OH \\ \diagdown OH\end{matrix}$$

isolating the labeled reaction products by thin layer chromatography and measuring the amount of radioactivity of the isolated labeled reaction products.

8. The method of claim 7 wherein an internal standard is used.

9. The method of claim 8 wherein the internal standard is $^{14}C$ labeled prostaglandin $F_{2\alpha}$.

* * * * *

UNITED STATES PATENT OFFICE
CERTIFICATE OF CORRECTION

PATENT NO. : 3,934,979

DATED : January 27, 1976

Page 1 of 2

INVENTOR(S) : William O. McClure

It is certified that error appears in the above-identified patent and that said Letters Patent are hereby corrected as shown below:

At Column 2, line 5: "where R is a radical containing a fluorescent of radio-" should read -- where R is a radical containing a fluorescent or radio- --

At Column 6, lines 12 and 13: "2. The method of claim 1 wherein R contains a fluorescent label." should read
-- 2. The method of claim 1 wherein R contains a radioactive label. --

At Column 6, lines 14 and 15: "3. The method of claim 1 wherein R contains a radioactive label." should read
-- 3. The method of claim 2 wherein the radioactive label is $^{14}C$ or $^{3}H$. --

At Column 6, lines 16 and 17: "4. The method of claim 3 wherein the radioactive label is $^{14}C$ or $^{3}H$." should read
-- 4. The method of claim 3 wherein R is a tritium labeled butyl radical. --

At Column 6, lines 18 and 19: "5. The method of claim 1 wherein R is a tritium labeled butyl radical." should read
-- 5. The method of claim 1 wherein R contains a fluorescent label. --

Continued --

UNITED STATES PATENT OFFICE
CERTIFICATE OF CORRECTION

PATENT NO. : 3,934,979
DATED : January 27, 1976
INVENTOR(S) : William O. McClure It is certified that error appears in the above-identified patent and that said Letters Patent are hereby corrected as shown below:

At Column 6, lines 22 thru 30:

Should read

— 7. A method for assaying prostaglandin $F_{2\alpha}$ comprising reacting a biological sample containing $PGF_{2\alpha}$ with $^{3}H-CH_{3}-CH_{2}-CH_{2}-CH_{2}-B{\overset{OH}{\underset{OH}{<}}}$ , isolating the labeled reaction products by thin layer chromatography and measuring the amount of radioactivity of the isolated labeled reaction products. —

Column 6, line 20, "claim 4" should read -- claim 5 --.

Signed and Sealed this

Twenty-second Day of February 1977

[SEAL]

Attest:

RUTH C. MASON
Attesting Officer

C. MARSHALL DANN
Commissioner of Patents and Trademarks